(12) United States Patent
Tomiyasu et al.

(10) Patent No.: US 10,381,396 B2
(45) Date of Patent: Aug. 13, 2019

(54) IMAGING PANEL AND X-RAY IMAGING DEVICE

(71) Applicant: Sharp Kabushiki Kaisha, Osaka (JP)

(72) Inventors: Kazuhide Tomiyasu, Osaka (JP); Shigeyasu Mori, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 405 days.

(21) Appl. No.: 15/321,132

(22) PCT Filed: Jun. 22, 2015

(86) PCT No.: PCT/JP2015/067882
§ 371 (c)(1),
(2) Date: Dec. 21, 2016

(87) PCT Pub. No.: WO2016/002562
PCT Pub. Date: Jan. 7, 2016

(65) Prior Publication Data
US 2017/0154915 A1 Jun. 1, 2017

(30) Foreign Application Priority Data
Jun. 30, 2014 (JP) ................................. 2014-134722

(51) Int. Cl.
*H01L 27/146* (2006.01)
*G01T 1/20* (2006.01)
(Continued)

(52) U.S. Cl.
CPC ....... *H01L 27/14663* (2013.01); *G01N 23/04* (2013.01); *G01T 1/20* (2013.01);
(Continued)

(58) Field of Classification Search
CPC ..... H01L 27/14678; G01T 1/208; G01T 1/24; G01T 1/003; G01T 1/2018
See application file for complete search history.

(56) References Cited

U.S. PATENT DOCUMENTS

2004/0104351 A1 6/2004 Shibayama
2009/0057564 A1 3/2009 Miyayama et al.
(Continued)

FOREIGN PATENT DOCUMENTS

JP 2002-124676 A 4/2002
JP 2006-156555 A 6/2006
(Continued)

OTHER PUBLICATIONS

U.S. Appl. No. 15/320,682, filed Dec. 20, 2016.
(Continued)

*Primary Examiner* — Don K Wong
(74) *Attorney, Agent, or Firm* — ScienBiziP, P.C.

(57) ABSTRACT

The present invention aims at inhibiting the occurrence of thinning or disconnecting of the bias wiring line in an imaging panel and X-ray imaging device, thereby inhibiting signal delays, signal transmission defects, and the like. A second contact hole electrically connecting an electrode of a photodiode to a bias wiring line penetrates a second interlayer insulating film and photosensitive resin layer. In the second contact hole, an area of a region where the photosensitive resin layer opens is smaller than an area of a region where the second interlayer insulating film opens.

9 Claims, 9 Drawing Sheets

(51) Int. Cl.
*G01N 23/04* (2018.01)
*H01L 27/12* (2006.01)
*H04N 5/32* (2006.01)

(52) U.S. Cl.
CPC ...... *H01L 27/124* (2013.01); *H01L 27/14632* (2013.01); *H01L 27/14687* (2013.01); *H04N 5/32* (2013.01)

(56) References Cited

U.S. PATENT DOCUMENTS

| | | |
|---|---|---|
| 2009/0078877 A1 | 3/2009 | Yaegashi et al. |
| 2009/0250699 A1 | 10/2009 | Okada |
| 2009/0267121 A1* | 10/2009 | Ishida ............... H01L 27/14658 257/292 |
| 2011/0133095 A1 | 6/2011 | Imai |
| 2011/0186853 A1 | 8/2011 | Terai et al. |
| 2012/0313103 A1 | 12/2012 | Yamada et al. |
| 2013/0264485 A1 | 10/2013 | Kawanabe et al. |
| 2013/0299711 A1 | 11/2013 | Mochizuki et al. |
| 2013/0307041 A1 | 11/2013 | Mochizuki et al. |
| 2014/0103347 A1 | 4/2014 | Ishino |
| 2017/0131413 A1 | 5/2017 | Tomiyasu et al. |
| 2017/0139056 A1 | 5/2017 | Tomiyasu et al. |
| 2017/0148843 A1 | 5/2017 | Mori et al. |
| 2017/0154914 A1 | 6/2017 | Tomiyasu et al. |
| 2017/0154916 A1 | 6/2017 | Mori et al. |
| 2017/0160403 A1 | 6/2017 | Tomiyasu et al. |

FOREIGN PATENT DOCUMENTS

| | | |
|---|---|---|
| JP | 2006-253481 A | 9/2006 |
| JP | 2007-103578 A | 4/2007 |
| JP | 2009-59975 A | 3/2009 |
| JP | 2009-94465 A | 4/2009 |
| JP | 2009-212120 A | 9/2009 |
| JP | 2009-252835 A | 10/2009 |
| JP | 2010-98329 A | 4/2010 |
| JP | 2011-124334 A | 6/2011 |
| JP | 2011-159908 A | 8/2011 |
| JP | 2013-16772 A | 1/2013 |
| JP | 2013-219067 A | 10/2013 |
| JP | 2013-235934 A | 11/2013 |
| JP | 2013-235935 A | 11/2013 |
| JP | 2014-78651 A | 5/2014 |

OTHER PUBLICATIONS

U.S. Appl. No. 15/321,129, filed Dec. 21, 2016.
U.S. Appl. No. 15/320,704, filed Dec. 20, 2016.
U.S. Appl. No. 15/321,127, filed Dec. 21, 2016.
U.S. Appl. No. 15/321,142, filed Dec. 21, 2016.
U.S. Appl. No. 15/320,712, filed Dec. 20, 2016.

* cited by examiner

<A-A Cross Section>

<B-B Cross Section>

<A-A Cross Section>   <B-B Cross Section>

<A-A Cross Section>   <B-B Cross Section>

<A-A Cross Section>

IMAGING PANEL AND X-RAY IMAGING DEVICE

TECHNICAL FIELD

The present invention relates to an imaging panel and an X-ray imaging device.

BACKGROUND ART

There are X-ray imaging devices that take X-ray images via an imaging panel having a plurality of pixels. In these types of X-ray imaging devices, photodiodes such as X-ray conversion films made of amorphous selenium (a-Se) convert the radiated X-rays into electric charge, for example. The electric charge that has been thus converted is read out by operating a thin film transistor (hereinafter, also "TFT") included in a pixel. Reading out the electric charge in this manner provides an X-ray image.

This type of X-ray imaging device is described in Patent Document 1, which discloses a photoelectric converter constituting an X-ray image detector. Patent Document 1 describes that, in this photoelectric converter, a photodiode element has a photoelectric conversion layer between a bottom electrode and top electrode, and the photoelectric conversion layer has a protective film formed smaller and more inside than the bottom electrode in a manner that covers at least the face of a pattern side wall of the photoelectric conversion layer.

RELATED ART DOCUMENT

Patent Document

Patent Document 1: Japanese Patent Application Laid-Open Publication No. 2014-78651

SUMMARY OF THE INVENTION

Problems to be Solved by the Invention

However, the contact hole described in Patent Document 1 has a level difference around the opening of the contact hole between the portion where the protective film opens and a portion where a second protective film opens in a layer above the protective film. Therefore, when a bias wiring line is formed covering the periphery of the opening of the contact hole, the bias wiring line is thinned at this level difference and becomes susceptible to disconnection and the like. This results in a risk of bias signal delays or signal transmission defects.

The present invention aims at inhibiting the occurrence of thinning or disconnecting of the bias wiring line in an imaging panel and X-ray imaging device, thereby inhibiting signal delays, signal transmission defects, and the like.

Means for Solving the Problems

An imaging panel of the present invention that solves the above-mentioned problems is an imaging panel for generating an image in accordance with scintillation light obtained from X-rays that have passed through a specimen, the imaging panel including: a substrate; a plurality of thin film transistors on the substrate; a first insulating film covering the thin film transistors; a plurality of conversion elements on the first insulating film that convert the scintillation light to electric charge; a second insulating film covering the plurality of conversion elements and the first insulating film, the second insulating film having a contact hole therein; a photosensitive resin layer on the second insulating film and in the contact hole of the second insulating film; and a bias wiring line respectively connecting to the conversion elements and supplying a bias voltage to the conversion elements, wherein each of the thin film transistors includes: a gate electrode; a gate insulating film in a layer above or a layer below the gate electrode; a semiconductor active layer facing the gate electrode with the gate insulating film interposed between the semiconductor active layer and the gate electrode; a source electrode electrically connected to the semiconductor active layer; and a drain electrode electrically connected to the semiconductor active layer and separated from the source electrode, wherein the plurality of conversion elements each include: a first semiconductor layer electrically connected to the drain electrode via a contact hole in the first insulating film; a second semiconductor layer over the first semiconductor layer and having a conductivity type that is opposite to the first semiconductor layer; and an electrode on the second semiconductor layer, and wherein a contact hole is formed in a portion of the photosensitive resin layer that is disposed within the contact hole in the second insulating film, and the electrode on the second semiconductor layer is connected to the bias wiring line via the contact hole in the portion of the photosensitive resin layer.

Effects of the Invention

The present invention makes it possible to inhibit the occurrence of thinning or disconnecting of the bias wiring line in an imaging panel and X-ray imaging device, thereby inhibiting signal delays, signal transmission defects, and the like.

DETAILED DESCRIPTION OF EMBODIMENTS

Figure 1:
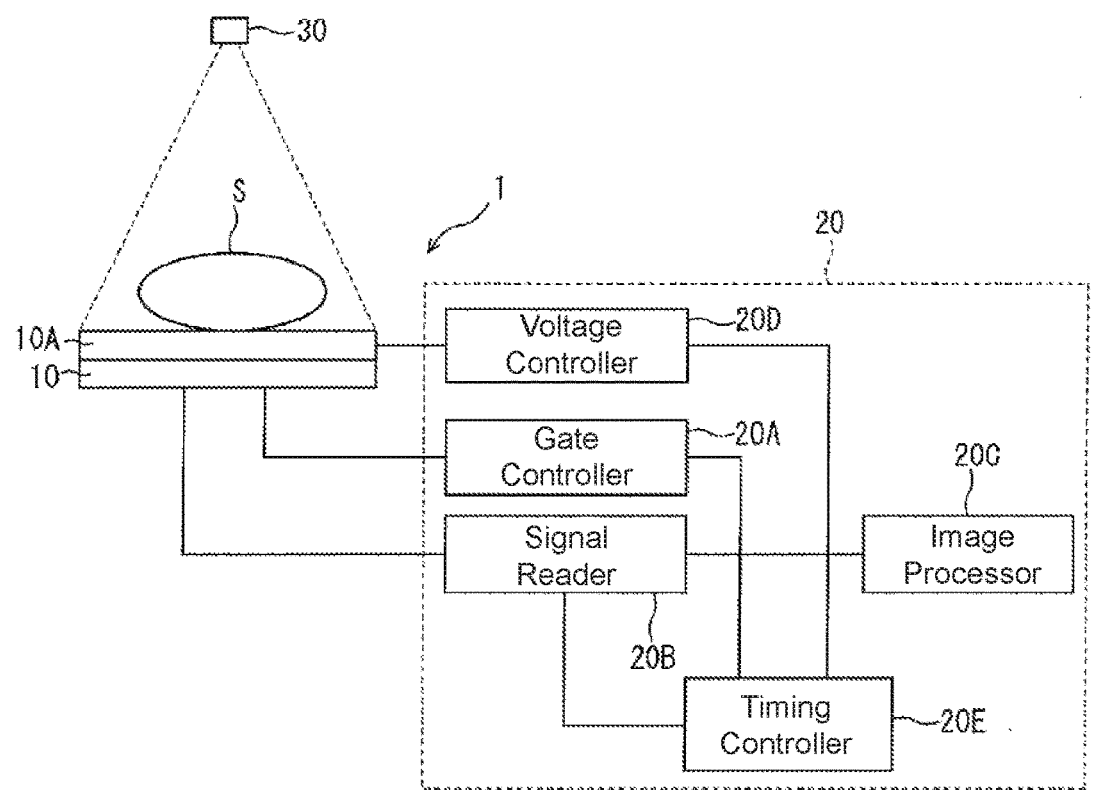
FIG. 1 is a schematic diagram showing an X-ray imaging device of an embodiment.

An imaging panel of one embodiment of the present invention is an imaging panel for generating an image in accordance with scintillation light obtained from X-rays that have passed through a specimen, the imaging panel including: a substrate; a plurality of thin film transistors on the substrate; a first insulating film covering the thin film transistors; a plurality of conversion elements on the first insulating film that convert the scintillation light to electric charge; a second insulating film covering the plurality of conversion elements and the first insulating film, the second insulating film having a contact hole therein; a photosensitive resin layer on the second insulating film and in the contact hole of the second insulating film; and a bias wiring line respectively connecting to the conversion elements and supplying a bias voltage to the conversion elements, wherein each of the thin film transistors includes: a gate electrode; a gate insulating film in a layer above or a layer below the gate electrode; a semiconductor active layer facing the gate electrode with the gate insulating film interposed between the semiconductor active layer and the gate electrode; a source electrode electrically connected to the semiconductor active layer; and a drain electrode electrically connected to the semiconductor active layer and separated from the source electrode, wherein the plurality of conversion elements each include: a first semiconductor layer electrically connected to the drain electrode via a contact hole in the first insulating film; a second semiconductor layer over the first semiconductor layer and having a conductivity type that is opposite to the first semiconductor layer; and an electrode on the second semiconductor layer, and wherein a contact hole is formed in a portion of the photosensitive resin layer that is disposed within the contact hole in the second insulating film, and the electrode on the second semiconductor layer is connected to the bias wiring line via the contact hole in the portion of the photosensitive resin layer (first configuration).

According to the first configuration, the second contact hole is formed penetrating the second insulating film and the photosensitive resin layer, and the area of the region where the photosensitive resin layer opens is smaller than the area of the region where the second insulating film opens. Thus, the portion where the second insulating film is opened does not form a level difference at the inner side face of the second contact hole. Accordingly, the opening peripheral section of the second contact hole only has a level difference at the portion where the photosensitive resin layer opens, which inhibits disconnecting, thinning, etc. of the bias wiring line at the second contact hole. As a result, it is possible to inhibit the occurrence of bias signal delay or signal transmission defects.

A second configuration is the first configuration, in which it is preferable that, in the contact hole, a periphery of the contact hole in the second insulating film be covered by the photosensitive resin layer.

A third configuration is the first or second configuration, in which the gate insulating film may be in a layer above the gate electrode.

A fourth configuration is the third configuration, in which the configuration may further include an etch-stop layer on the semiconductor active layer.

A fifth configuration is the first or second configuration, in which the gate insulating film may be in a layer below the gate electrode.

An X-ray imaging device of one embodiment of the present invention includes the imaging panel according to any one of the first to fifth configurations; a controller controlling respective gate voltages of the plurality of thin film transistors and reading out data signals that correspond to electric charge converted by the conversion elements; an X-ray light source radiating X-rays; and a scintillator converting the X-rays to scintillation light (sixth configuration).

Embodiments of the present invention will be described in detail below with reference to the drawings. Portions in the drawings that are the same or similar are assigned the same reference characters and descriptions thereof will not be repeated.

(Configuration)

FIG. 1 is a schematic diagram showing an X-ray imaging device of an embodiment. An X-ray imaging device 1 includes an imaging panel 10 and a controller 20. X-rays from the X-ray source 30 irradiate a specimen S, and the X-rays that have passed through the specimen S are converted to fluorescent light (hereinafter, scintillator light) by the scintillator 10A at the top of the imaging panel 10. The X-ray imaging device 1 captures X-ray images by the scintillator light being imaged by the imaging panel 10 and the controller 20.

Figure 2:
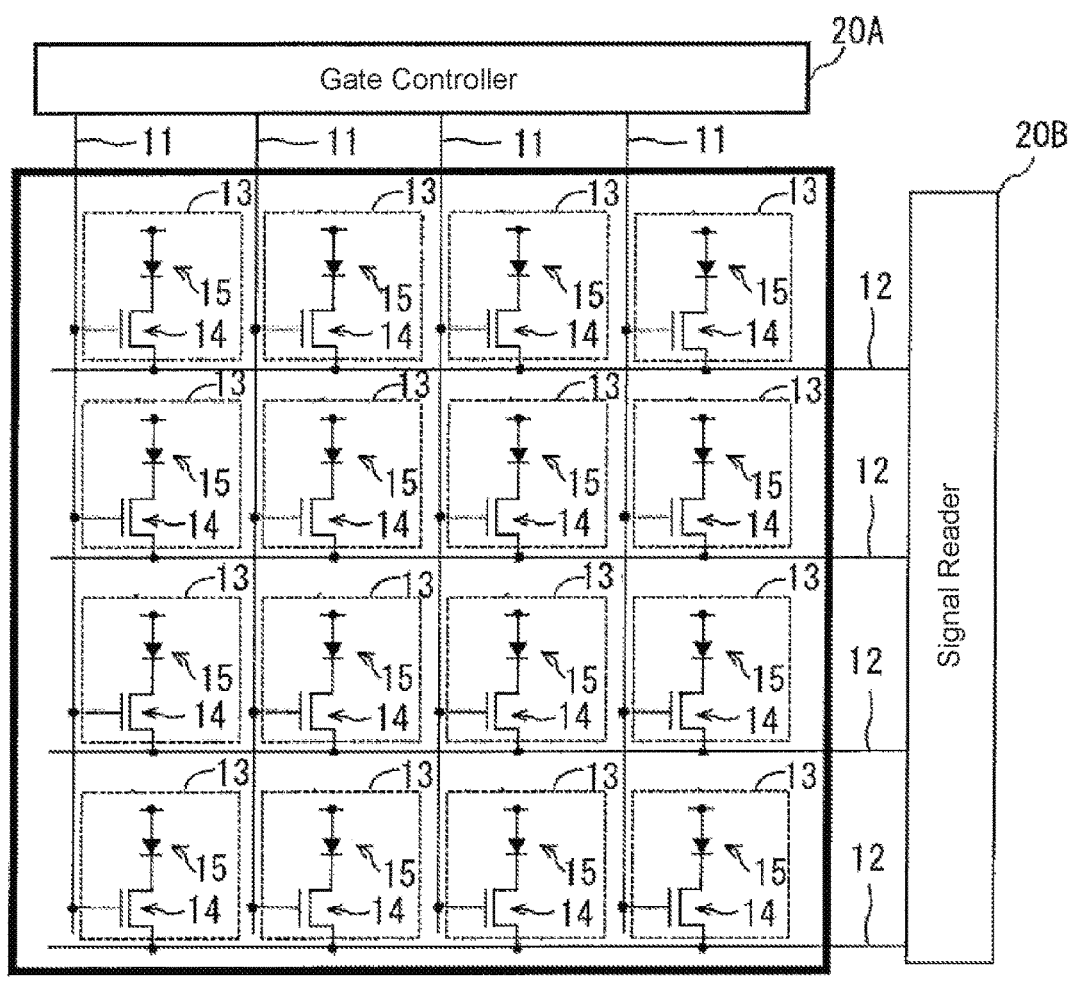
FIG. 2 is a schematic diagram showing a general configuration of the imaging panel in FIG. 1.

FIG. 2 is a schematic diagram showing a general configuration of the imaging panel 10. As shown in FIG. 2, a plurality of gate lines 11 and a plurality of data lines 12 intersecting the plurality of gate lines 11 are formed on the imaging panel 10. The imaging panel 10 has a plurality of pixels 13 defined by the gate lines 11 and data lines 12. FIG. 2 shows an example that has 16 (four rows and four columns) pixels 13, but the number of pixels in the imaging panel 10 is not limited to this.

Each of the pixels 13 has a TFT 14 connected to the gate line 11 and data line 12, and a photodiode 15 connected to the TFT 14. Furthermore, while not shown in FIG. 2, each of the pixels 13 has a bias line 16 (see FIG. 3) that supplies bias voltage to the photodiode 15, and this bias line is disposed roughly parallel to the data line 12.

In each of the pixels 13, the scintillation light, or namely the converted X-rays that have passed through the specimen S, is converted by the photodiode 15 into an electric charge that corresponds to the intensity of the scintillation light.

Each of the gate lines 11 in the imaging panel 10 is switched to a sequentially selectable state by the gate controller 20A, and the TFT 14 connected to the gate line 11 in the selected state turns ON. When the TFT 14 turns ON, a data signal corresponding to the electric charge converted by the photodiode 15 is output via the data line 12.

Figure 3:
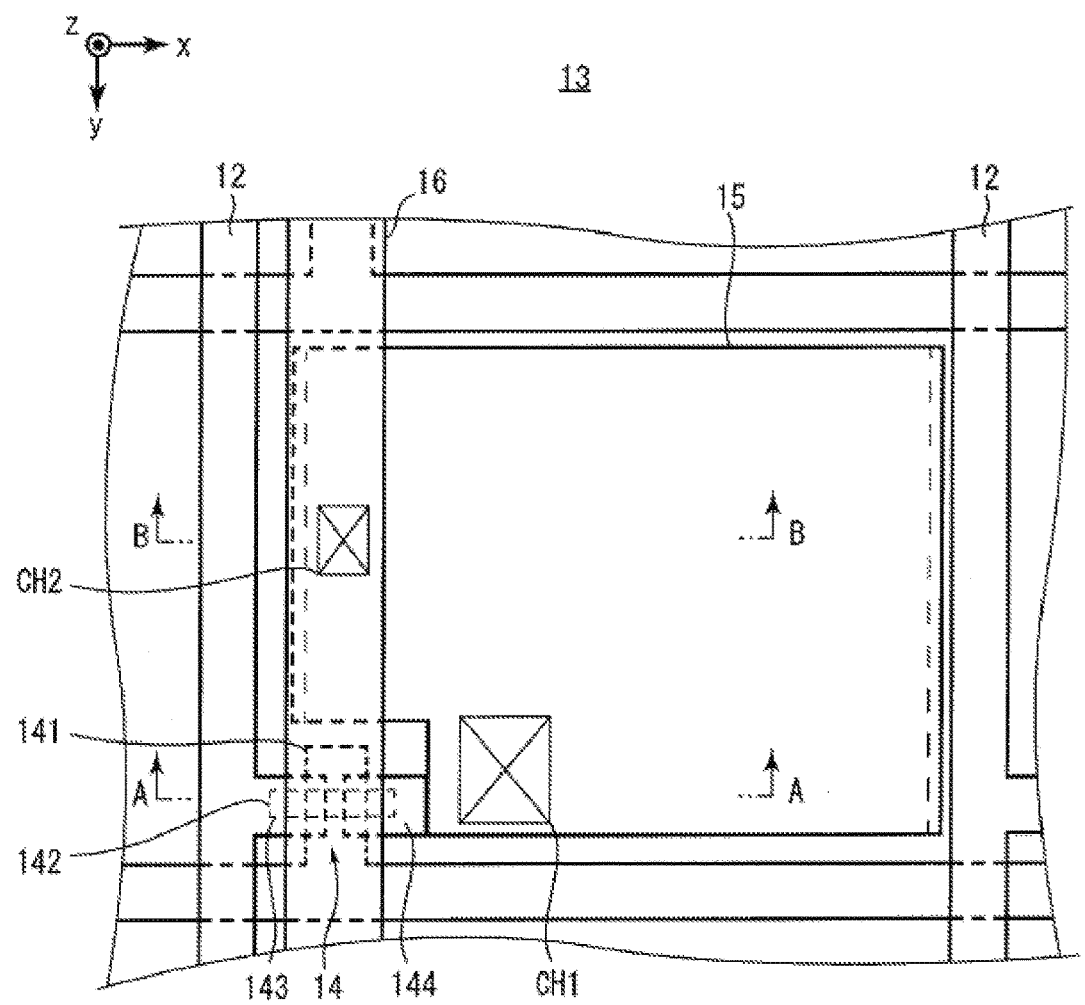
FIG. 3 is a plan view of a pixel from the imaging panel in FIG. 2.
Figure 4A:
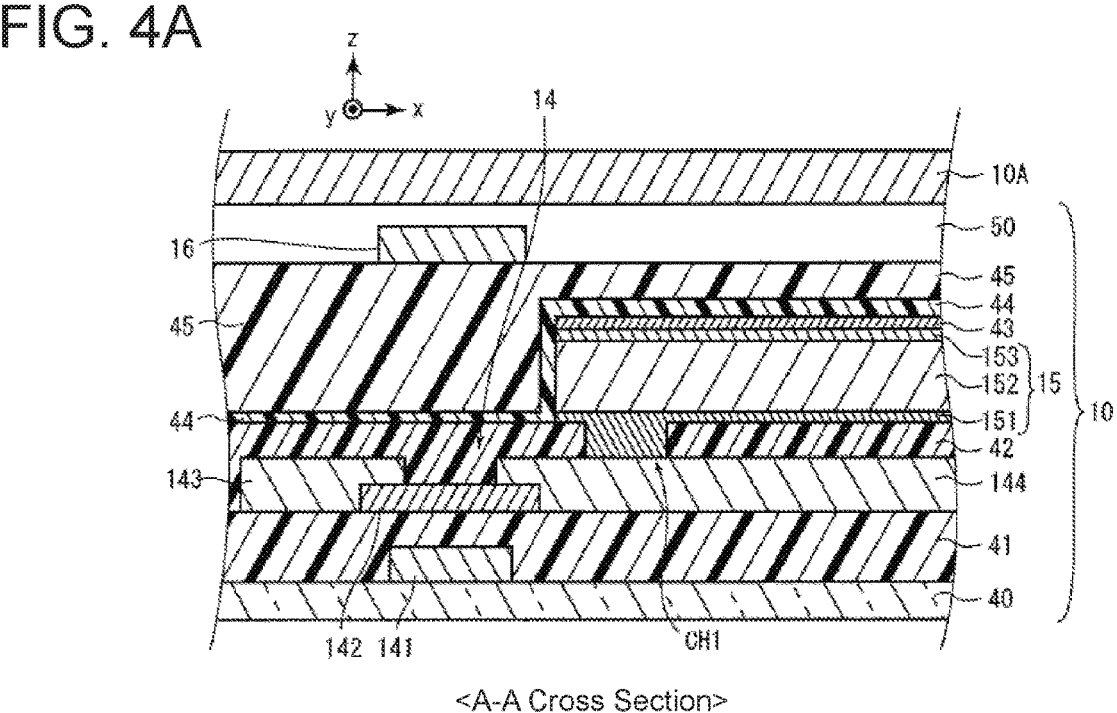
FIG. 4A is a cross-sectional view of FIG. 3 along the line A-A.

Next, a specific configuration of the pixel 13 will be described. FIG. 3 is a plan view of the pixel 13 from the imaging panel 10 shown in FIG. 2. FIG. 4A is a cross-sectional view of the pixel 13 shown in FIG. 3 along the line A-A, and FIG. 4B is a cross-sectional view of the pixel 13 shown in FIG. 3 along the line B-B.

Figure 4B:
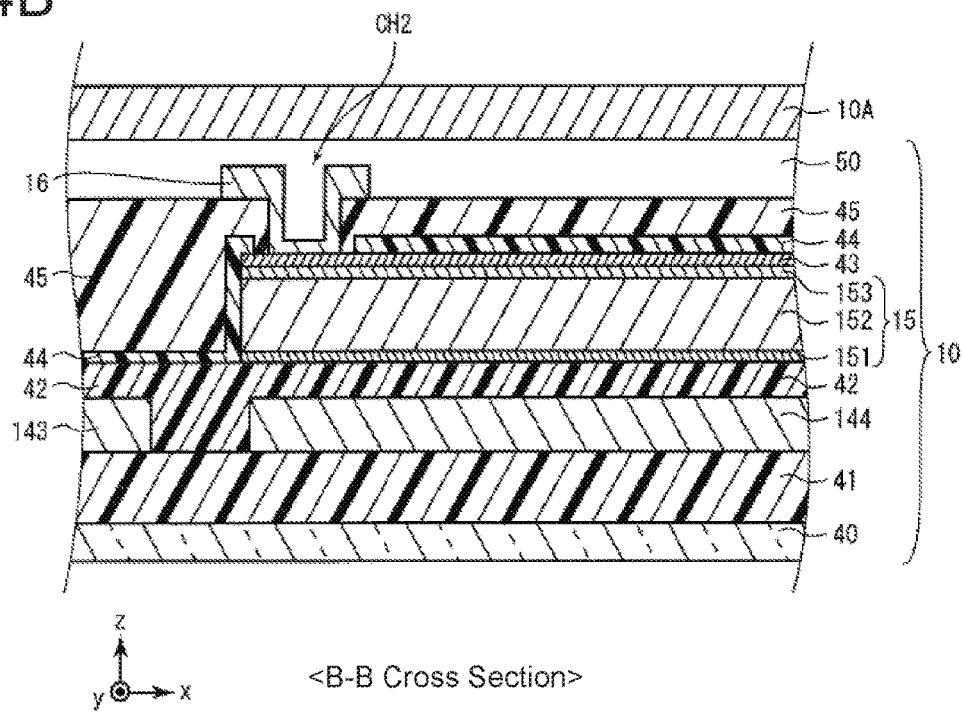
FIG. 4B is a cross-sectional view of FIG. 3 along the line B-B.

As shown in FIG. 4A and FIG. 4B, the pixel 13 is formed on a substrate 40. The substrate 13 is an insulating substrate such as a glass substrate, silicon substrate, a heat-resistant plastic substrate, a resin substrate, or the like, for example. In particular, for a plastic substrate or resin substrate, polyethyleneterephthalate (PET), polyethylene naphthalate (PEN), polyethersulfone (PES), acrylic, polyimide, or the like may be used.

The TFT 14 includes a gate electrode 141, semiconductor active layer 142 disposed on the gate electrode 141 with a gate insulating film 41 therebetween, and a source electrode 143 and drain electrode 144 connected to the semiconductor active layer 142.

The gate electrode 141 is formed contacting one surface (hereinafter, main surface) of the substrate 40 in the thickness direction. The gate electrode 141 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The gate electrode 141 may also be constituted by a plurality of metal films layered together, for example. In the present embodiment, the gate electrode 141 has a layered structure in which an aluminum metal film and titanium metal film are layered together in this order.

As shown in FIG. 4A, the gate insulating film 41 is formed on the substrate 40 and covers the gate electrode 141. The gate insulating film 41 may be silicon oxide ($SiO_x$), silicon nitride ($SiN_x$), silicon oxynitride ($SiO_xN_y$) ($x>y$), silicon nitrogen oxide ($SiN_xO_y$) ($x>y$), or the like, for example.

In order to prevent diffusion of impurities or the like from the substrate 40, the gate insulating film 41 may be a multilayer structure. For example, the lower layer may be silicon nitride ($SiN_x$), silicon nitrogen oxide ($SiN_xO_y$) ($x>y$), etc., and the upper layer may be silicon oxide ($SiO_x$), silicon oxynitride ($SiO_xN_y$) ($x>y$), etc. Moreover, in order to form a compact gate insulating film that has little gate leakage current at low formation temperatures, a noble gas such as Argon may be included in the reactive gas so as to be mixed into the insulating film. In the present embodiment, the gate insulating film 41 has a multilayer structure in which the bottom layer is a 100 nm-400 nm silicon nitride film formed with a reactant gas of $SiH_4$ and $NH_3$, and the top layer is a 50 nm-100 nm silicon oxide film.

As shown in FIG. 4A, the semiconductor active layer 142 is formed contacting the gate insulating film 41. The semiconductor active layer 142 is made of an oxide semiconductor. The oxide semiconductor may be an amorphous oxide semiconductor or the like containing $InGaO_3(ZnO)_5$, magnesium zinc oxide ($Mg_xZn_{1-x}O$), cadmium zinc oxide ($Cd_xZn_{1-x}O$), cadmium oxide (CdO), or containing prescribed proportions of indium (In), gallium (Ga), and zinc (Zn), for example. The semiconductor active layer 142 may be a ZnO amorphous material doped with one or more impurity elements selected among group 1 elements, group 13 elements, group 14 elements, group 15 elements, group 17 elements, and the like, or a polycrystalline material. Alternatively, the semiconductor active layer be a microcrystalline material (a mix of amorphous and polycrystalline states), or a material that has had no impurities added.

As shown in FIG. 4A and FIG. 4B, the source electrode 143 and drain electrode 144 are formed contacting the semiconductor active layer 142 and the gate insulating film 41. As shown in FIG. 3, the source electrode 143 is connected to the data line 12. As shown in FIG. 4A, the drain electrode 144 is connected to a photodiode 15 via a first contact hole CH1. The source electrode 143, data line 12, and drain electrode 144 are formed on the same layer.

The source electrode 143, data line 12, and drain electrode 144 are made of a metal such as aluminum (Al), tungsten (W), molybdenum (Mo), tantalum (Ta), chromium (Cr), titanium (Ti), or copper (Cu), or are an alloy of these metals or a metal nitride of these, for example. Alternatively, the source electrode 143, data line 12, and drain electrode 144 may be a transmissive material such as indium tin oxide (ITO), indium zinc oxide (IZO), indium tin oxide containing silicon oxide (ITSO), indium oxide ($In_2O_3$), tin oxide ($SnO_2$), zinc oxide (ZnO), titanium nitride, or the like, or may be a combination of these.

The source electrode 143, data line 12, and drain electrode 144 may be constituted by a plurality of metal films layered together, for example. In the present embodiment, the source electrode 143, data line 12, and drain electrode 144 have a multilayer structure in which a titanium metal film, aluminum metal film, and titanium metal film are layered together in this order.

As shown in FIGS. 4A and 4B, the first interlayer insulating film 42 covers the semiconductor active layer 142, source electrode 143, data line 12, and drain electrode 144. The first interlayer insulating film 42 may be a single layer structure made of silicon oxide ($SiO_2$) or silicon nitride (SiN), or a multilayer structure in which silicon nitride (SiN) and silicon oxide ($SiO_2$) are layered together in this order.

As shown in FIG. 4A and FIG. 4B, the photodiode 15 is formed on the first interlayer insulating film 42 contacting the drain electrode 144. The photodiode 15 includes at least a first semiconductor layer having a first conductivity type, and a second semiconductor layer having a second conductivity type that is opposite to the first conductivity type. In the present embodiment, the photodiode 15 includes an n-type amorphous silicon layer 151 (first semiconductor layer), intrinsic amorphous silicon layer 152, and a p-type amorphous silicon layer 153 (second semiconductor layer).

The n-type amorphous silicon layer 151 is made of amorphous silicon that has been doped with an n-type impurity (phosphorous, for example). The n-type amorphous silicon layer 151 is formed contacting the drain electrode 144. The thickness of the n-type amorphous silicon layer 151 is 20 nm to 100 nm, for example.

The intrinsic amorphous silicon layer 152 is made of intrinsic amorphous silicon. The intrinsic amorphous silicon layer 152 is formed contacting the n-type amorphous silicon layer 151. The thickness of the intrinsic amorphous silicon layer is 200 nm to 2000 nm, for example.

The p-type amorphous silicon layer 153 is made of amorphous silicon that has been doped with a p-type impurity (boron, for example). The p-type amorphous silicon layer 153 is formed contacting the intrinsic amorphous silicon layer 152. The thickness of the p-type amorphous silicon layer 153 is 10 nm to 50 nm, for example.

The drain electrode 144 functions as the drain electrode of the TFT 14 and the bottom electrode of the photodiode 15. Furthermore, the drain electrode 144 also functions as a reflective film that reflects scintillation light that has passed through the photodiode 15 back toward the photodiode 15.

As shown in FIG. 4A and FIG. 4B, an electrode 43 is formed on top of the photodiode 15 and functions as the top electrode of the photodiode 15. The electrode 43 is made of indium zinc oxide (IZO), for example.

The second interlayer insulating film 44 is formed contacting the first interlayer insulating film 42 and electrode 43. The second interlayer insulating film 44 may be a single layer structure made of silicon oxide ($SiO_2$) or silicon nitride (SiN), or a multilayer structure in which silicon nitride (SiN) and silicon oxide ($SiO_2$) are layered together in this order.

A photosensitive resin layer 45 is formed on top of the second interlayer insulating film 44. The photosensitive resin layer 45 is made of an organic resin material or an inorganic resin material.

As shown in FIGS. 3, 4A, and 4B, the bias wiring line 16 is formed on the photosensitive resin layer 45 substantially parallel to the data line 12. Specifically, as shown in FIGS. 4A and 4B, the bias wiring line 16 is formed on top of the photosensitive resin layer 45 so as to overlap the TFT 14 and be near an edge portion of the photodiode 15 near the data line 12. The bias wiring line 16 is connected to a voltage controller 20D (see FIG. 1). Furthermore, as shown in FIG. 4B, the bias wiring line 16 is connected to the electrode 43 via a second contact hole CH2 and applies a bias voltage received from the voltage controller 20D to the electrode 43. The bias wiring line 16 has a multilayer structure in which indium zinc oxide (IZO) and molybdenum (Mo) are layered together, for example.

Figure 5:
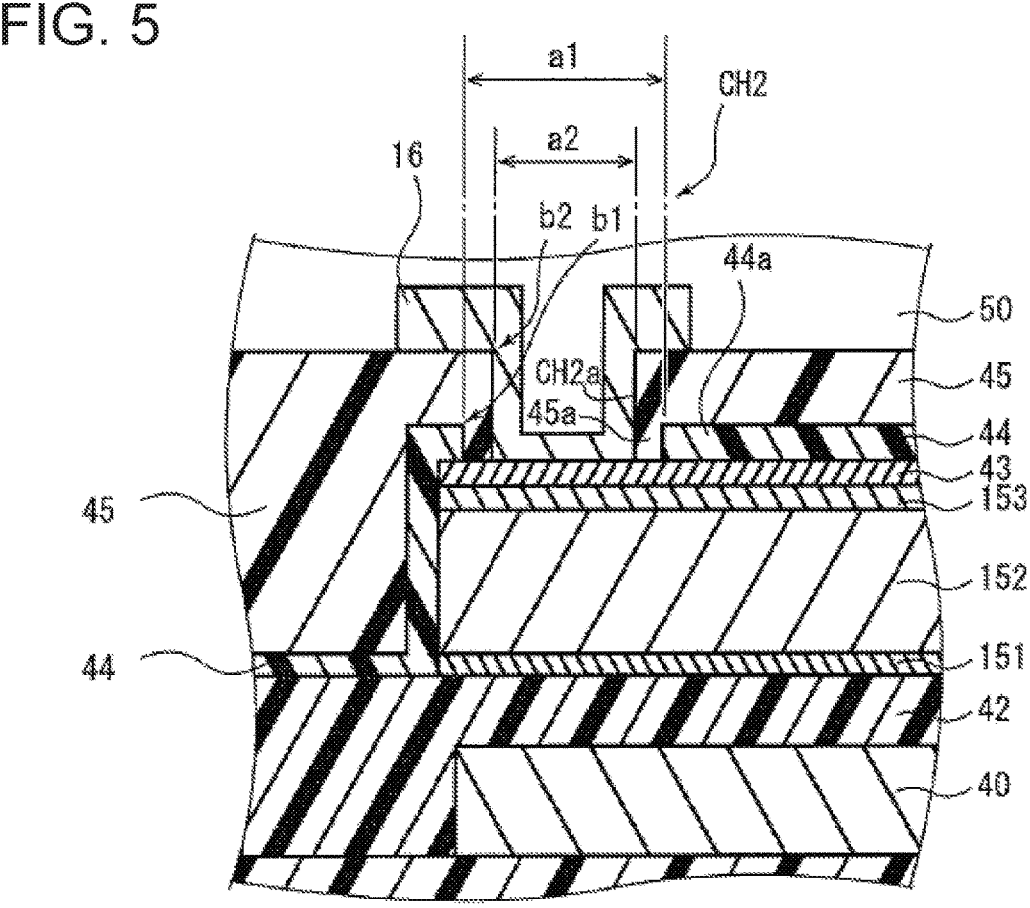
FIG. 5 is an enlarged view of primary components showing the contact hole periphery in FIG. 4B.

FIG. 5 is an enlarged view of primary components showing the second contact hole CH2 periphery in FIG. 4B. In the second contact hole CH2, the area of the open region of the second interlayer insulating film (the region shown by a1 in FIG. 5) is greater than the area of the open region of the photosensitive resin layer 45 (the region shown by a2 in FIG. 5). Thus, the hole peripheral section 44a near where the second interlayer insulating film 44 opens is completely covered by the hole peripheral section 45a near where the photosensitive resin layer 45 opens. In other words, a side face CH2a inside the second contact hole CH2 is covered by the photosensitive resin layer 45.

As shown in FIGS. 4A and 4B, a protective layer 50 is formed on top of the imaging panel 10, or namely on top of the photosensitive resin layer 45, so as to cover the bias wiring line 16, and the scintillator 10A is disposed on top of the protective layer 50.

The configuration of the controller 20 will be explained while referring back to FIG. 1. The controller 20 includes a gate controller 20A, signal reader 20B, image processor 20C, voltage controller 20D, and timing controller 20E.

As shown in FIG. 2, the gate controller 20A is connected to a plurality of the gate lines 11. The gate controller 20A applies, via the gate lines 11, a prescribed gate voltage to the TFTs 14 of the pixels 13 connected to the gate lines 11.

As shown in FIG. 2, the signal reader 20B is connected to the plurality of data lines 12. The signal reader 20B, via the respective data lines 12, reads out data signals that correspond to the electric charge converted by the photodiode 15 of the pixel 13. The signal reader 20B generates image signals based on the data signals and outputs the result to the image processor 20C.

The image processor 20C generates X-ray images based on the image signals output from the signal reader 20B.

The voltage controller 20D is connected to the bias wiring line 16. The voltage controller 20D applies a prescribed bias voltage to the bias wiring line 16. This applies a bias voltage to the photodiode 15 via the electrode 43 connected to the bias wiring line 16.

The timing controller 20E controls the operation timing of the gate controller 20A, signal reader 20B, and voltage controller 20D.

The gate controller 20A selects one gate line 11 from the plurality of gate lines 11 based on the control signal from the timing controller 20E. The gate controller 20A applies, via the selected gate line 11, a prescribed gate voltage to the TFT 14 of the pixel 13 connected to the corresponding gate line 11.

The signal reader 20B selects one data line 12 from the plurality of data lines 12 based on the control signal from the timing controller 20E. The signal reader 20B, via the selected data line 12, reads out the data signal corresponding to the electric charge converted by the photodiode 15 of the pixel 13. The pixel 13 where the data signal has been read out is connected to the data line 12 selected by the signal reader 20B and connected to the gate line 11 selected by the gate controller 20A.

When irradiated by X-rays from the X-ray source 30, the timing controller 20E outputs a control signal to the voltage controller 20D, for example. Based on this control signal, the voltage controller 20D applies a prescribed bias voltage to the electrode 43.

(Operation of X-Ray Imaging Device 10)

First, X-rays are radiated from the X-ray source 30. At such time, the timing controller 20E outputs a control signal to the voltage controller 20D. Specifically, a signal indicating that X-rays have been radiated from the X-ray source 30 is output from a controller that controls operation of the X-ray light source 30 to the timing controller 20E, for example. When this signal has been received by the timing controller 20E, the timing controller 20E outputs a control signal to the voltage controller 20D. The voltage controller 20D applies a prescribed voltage (bias voltage) to the bias wiring line 16 based on the control signal from the timing controller 20E.

The X-rays radiated from the X-ray source 30 pass through the specimen S and enter the scintillator 10A. The X-rays that have entered the scintillator 10A are converted into fluorescent light (scintillation light), and the scintillation light enters the imaging panel 10.

When the scintillation light enters the photodiode 15 disposed in the respective pixels 13 in the imaging panel 10, the photodiode 15 converts the scintillation light into an electric charge that corresponds to the intensity of the scintillation light.

The data signal that corresponds to the electric charge converted by the photodiode 15 passes through the data line 12 and is read out by the signal reader 20B when a gate voltage (plus voltage) received from the gate controller 20A via the gate line 11 turns ON the TFT 14. An X-ray image that corresponds to the read-out data signal is generated by the image processor 20C.

(Manufacturing Method of Imaging Panel 10)

Next, a method of manufacturing the imaging panel 10 will be explained. FIGS. 6 to 13 are cross-sectional views of the pixel 13 along lines A-A and B-B during each manufacturing step of the imaging panel 10.

Figure 6:
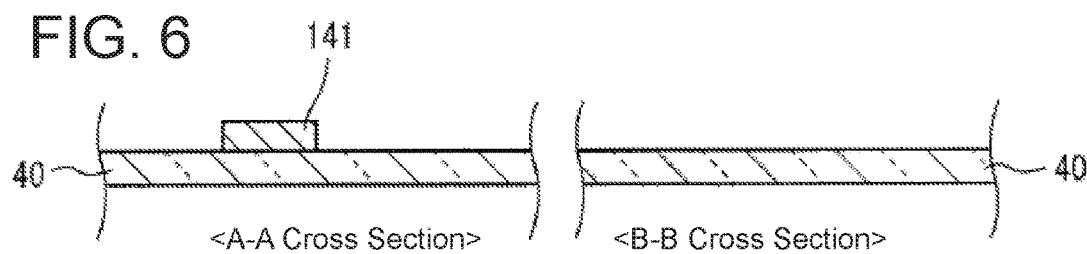
FIG. 6 is a cross-sectional view of a pixel in the manufacturing process of the gate electrode along the line A-A and along the line B-B.

As shown in FIG. 6, sputtering or the like is used to form an aluminum/titanium layered metal film on the substrate 40. Thereafter, photolithography is used to pattern this metal film to form the gate electrode 141 and gate line 11. The thickness of the metal film is 300 nm, for example.

Figure 7:
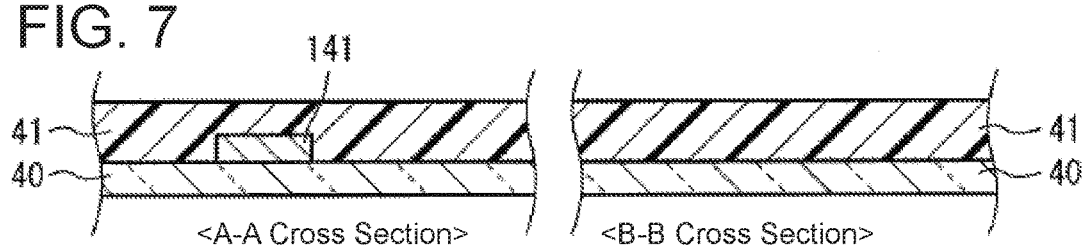
FIG. 7 is a cross-sectional view during a manufacturing process of a gate insulating film of the pixel shown in FIG. 3 along the line A-A and along the line B-B.

Next, as shown in FIG. 7, plasma-enhanced CVD or sputtering etc. is used to form the gate insulating film 41 made of silicon oxide ($SiO_x$) or silicon nitride ($SiN_x$) etc. on the substrate 40 so as to cover the gate electrode 141. The thickness of the gate insulating film 41 is approximately 20-150 nm, for example.

Figure 8:
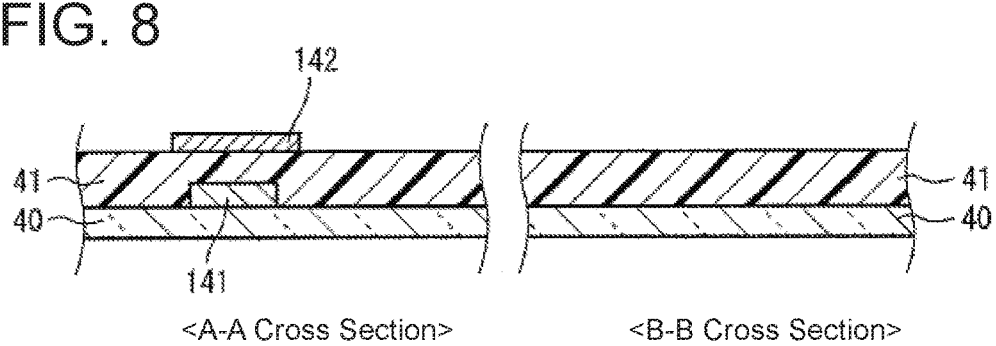
FIG. 8 is a cross-sectional view during a manufacturing process of a semiconductor active layer of the pixel shown in FIG. 3 along the line A-A and along the line B-B.

Next, as shown in FIG. 8, sputtering etc. is used to form an oxide semiconductor on the gate insulating film 41, and photolithography is used to pattern the oxide semiconductor to form the semiconductor active layer 142, for example. After the semiconductor active layer 142 has been formed, a high-temperature heat treatment (350° C. or greater, for example) is performed in an environment containing oxygen (e.g., the atmosphere). In such a case, it is possible to reduce oxygen defects in the semiconductor active layer 142. The thickness of the semiconductor active layer 142 is 30 nm to 100 nm, for example.

Figure 9:
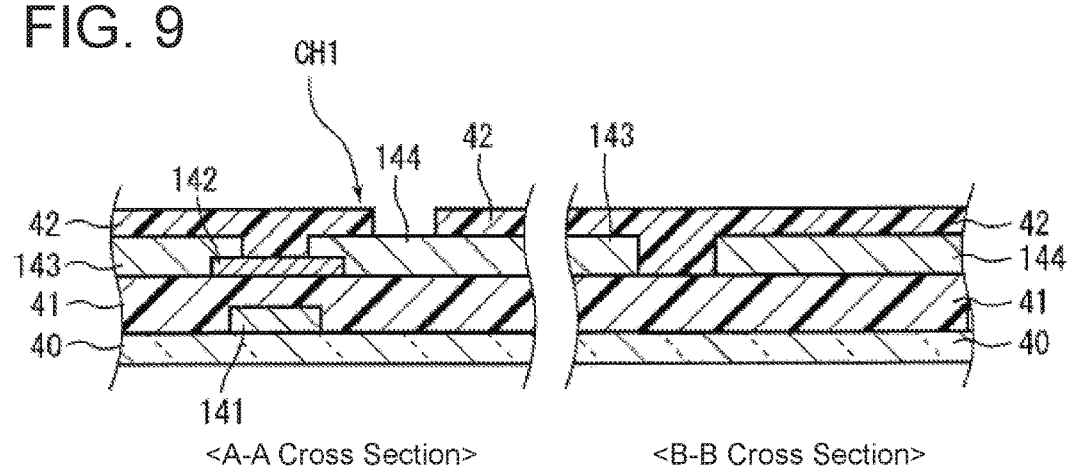
FIG. 9 is a cross-sectional view during a manufacturing process of a source electrode and a drain electrode of the pixel shown in FIG. 3 along the line A-A and along the line B-B.

Next, as shown in FIG. 9, sputtering or the like used to layer titanium, aluminum, and titanium metal films in this order on the gate insulating film 41 and semiconductor active layer 142. Thereafter, photolithography is used to pattern this metal film to form the source electrode 143, data line 12, and drain electrode 144. The thickness of the source electrode 143, data line 12, and drain electrode 144 is 50 nm to 500 nm, for example. The etching may be either dry etching or wet etching, with dry etching being suitable if the area of the substrate 40 is large. This forms a bottom-gate TFT 14.

Next, plasma-enhanced CVD is used to form the silicon oxide ($SiO_2$) or silicon nitride (SiN) first interlayer insulating film 42 on the source electrode 143, data line 12, and drain electrode 144, for example. Thereafter, a thermal treatment of approximately 350° C. is performed on the entire surface of the substrate 40, and photolithography is used to pattern the first interlayer insulating film 42 and form the first contact hole CH1.

Figure 10:
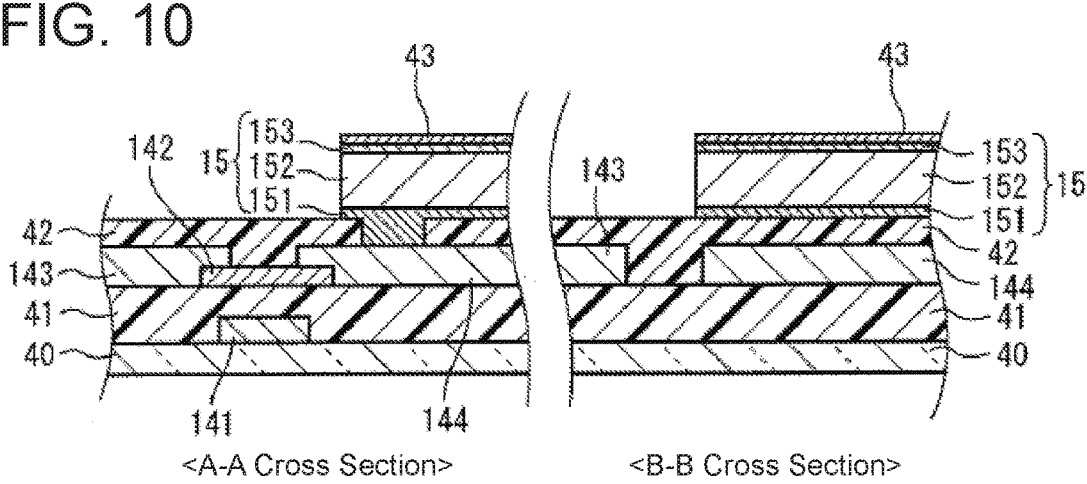
FIG. 10 is a cross-sectional view during a manufacturing process of a photodiode of the pixel shown in FIG. 3 along the line A-A and along the line B-B.

Next, as shown in FIG. 10, sputtering or the like is used to form the n-type amorphous silicon layer 151, intrinsic amorphous silicon layer 152, and p-type amorphous silicon layer 153 in this order on the first interlayer insulating film 42 and drain electrode 144. At such time, the drain electrode 144 electrically connects to the n-type amorphous silicon layer 151 via the first contact hole CH1. Thereafter, photolithography is used for patterning, and dry etching is performed to form the photodiode 15.

Next, sputtering or the like is used to deposit indium zinc oxide (IZO) on the first interlayer insulating film 42 and photodiode 15, which is patterned by photolithography to form the electrode 43.

Figure 11:
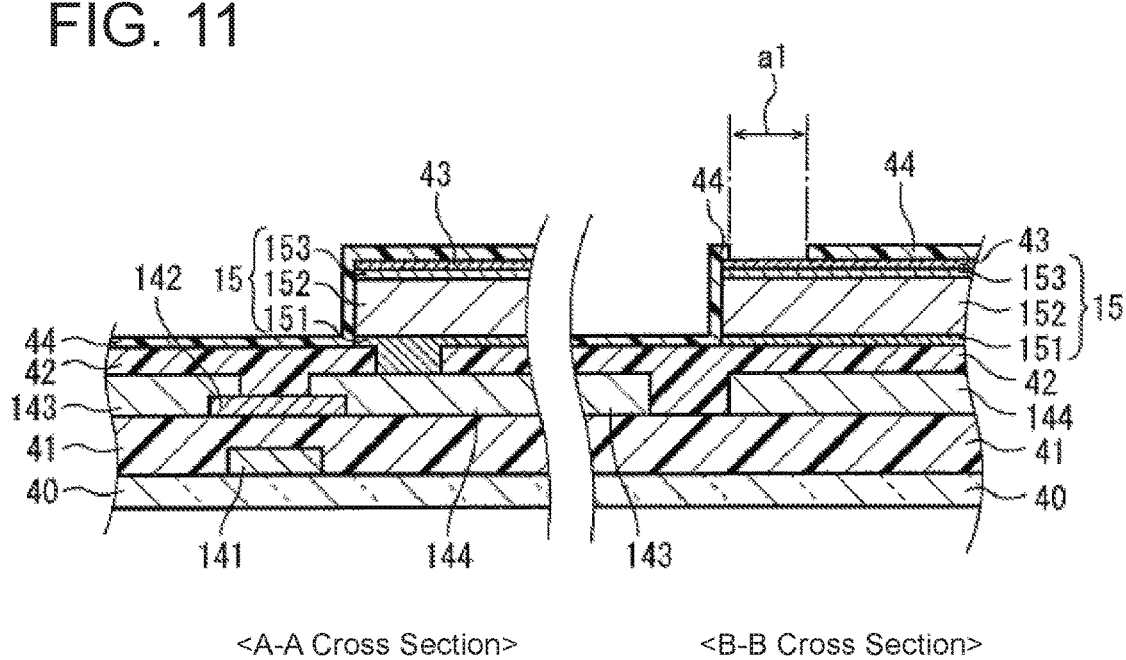
FIG. 11 is a cross-sectional view during a manufacturing process of a second interlayer insulating film of the pixel shown in FIG. 3 along the line A-A and along the line B-B.

Next, as shown in FIG. 11, plasma-enhanced CVD or the like is used to deposit silicon oxide ($SiO_2$) or silicon nitride (SiN) on the first interlayer insulating film 42 and electrode 43 to form the second interlayer insulating film 44. Thereafter, photolithography is used for patterning in order to form the opening that serves as the second contact hole CH2 on the electrode 43.

Figure 12:
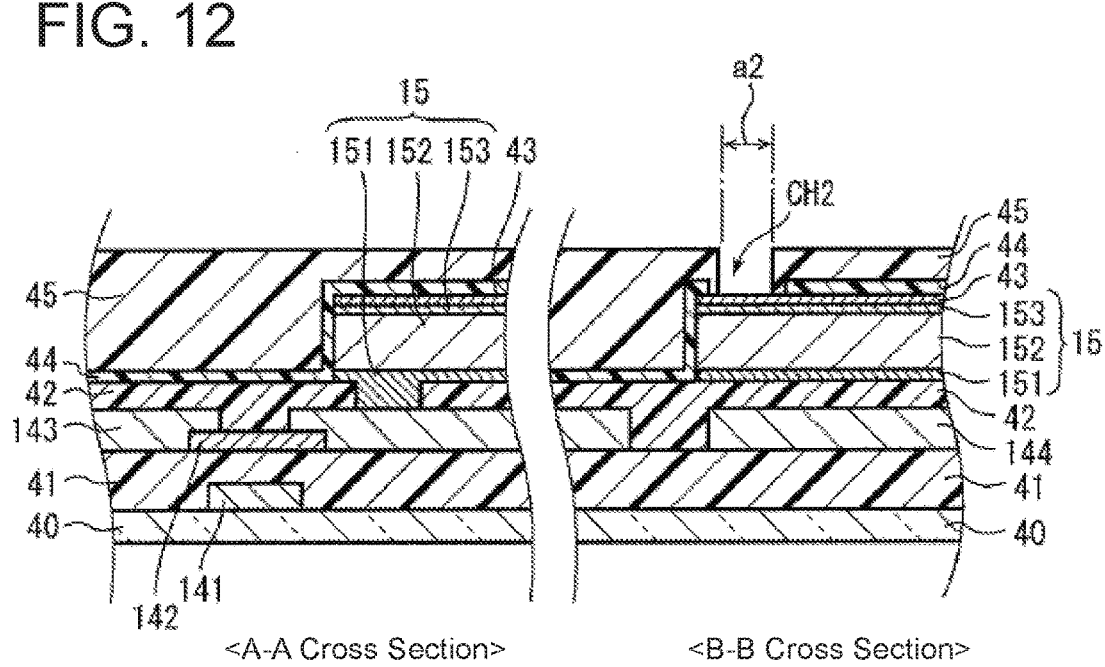
FIG. 12 is a cross-sectional view during a manufacturing process of a photosensitive resin layer of the pixel shown in FIG. 3 along the line A-A and along the line B-B.

Next, as shown in FIG. 12, a photosensitive resin is deposited on the second interlayer insulating film 44 and dried to form the photosensitive resin layer 45, and then photolithography is used to form an opening. This forms the second contact hole CH2, which penetrates the second interlayer insulating film 44 and photosensitive resin layer 45.

Figure 13:
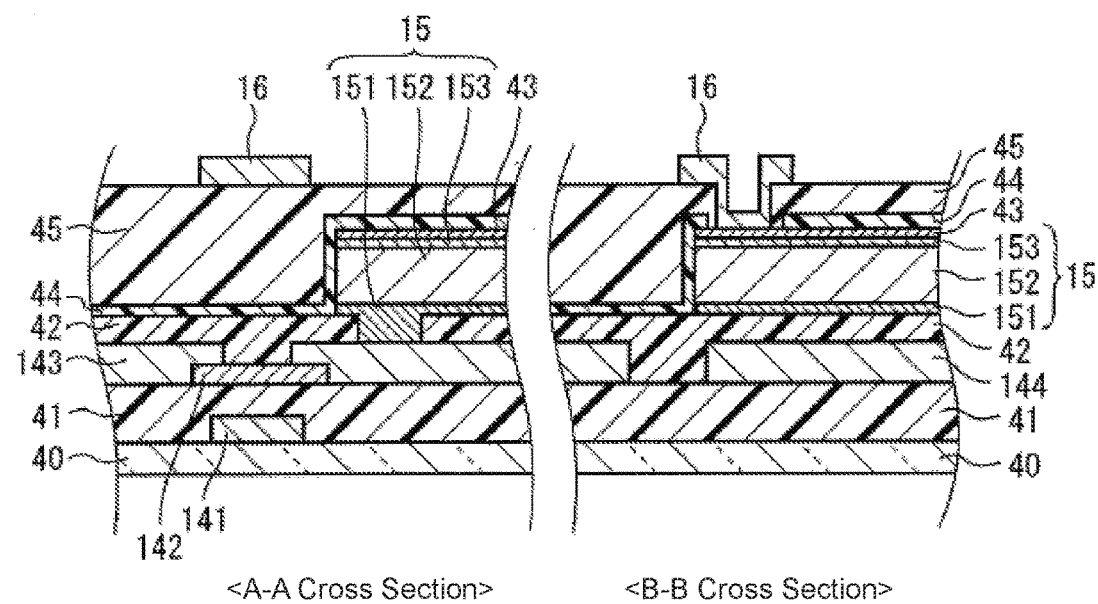
FIG. 13 is a cross-sectional view during a manufacturing process of a photosensitive resin layer and bias wiring line of the pixel shown in FIG. 3 along the line A-A and along the line B-B.

Then, as shown in FIG. 13, sputtering or the like is used to deposit indium tin oxide (IZO) and molybdenum (Mo) metal film layers on the photosensitive resin layer 45, and these are patterned by photolithography to form the bias wiring line 16.

In the present embodiment, the second contact hole CH2 is formed penetrating the second interlayer insulating film 44 and photosensitive resin layer 45. As shown in FIG. 5, the area of the region a2 where the photosensitive resin layer 45 opens has a smaller size than the area of the region a1 where the second interlayer insulating film 44 opens. Thus, a level difference b1 constituted by the hole peripheral section 44a near where the second interlayer insulating film 44 opens does not affect the shape of the side face CH2a inside the second contact hole CH2. This is because the hole peripheral section 44a near where the second interlayer insulating film 44 opens is completely covered by the hole peripheral section 45a near where the photosensitive resin layer 45 opens. In other words, the shape of the side face CH2a of the second contact hole CH2 is influenced only by a level difference b2 constituted by the hole peripheral section 45a of the photosensitive resin layer 45.

Accordingly, the present embodiment inhibits disconnection, thinning, etc. of the bias wiring line at the second contact hole CH2 more than if the shape of the side face CH2a of the second contact hole CH2 were influenced by both of the level differences b1 and b2. As a result, it is possible to inhibit the occurrence of bias signal delay or signal transmission defects.

Modification Examples

Next, modification examples of the present invention will be explained.

Figure 14:
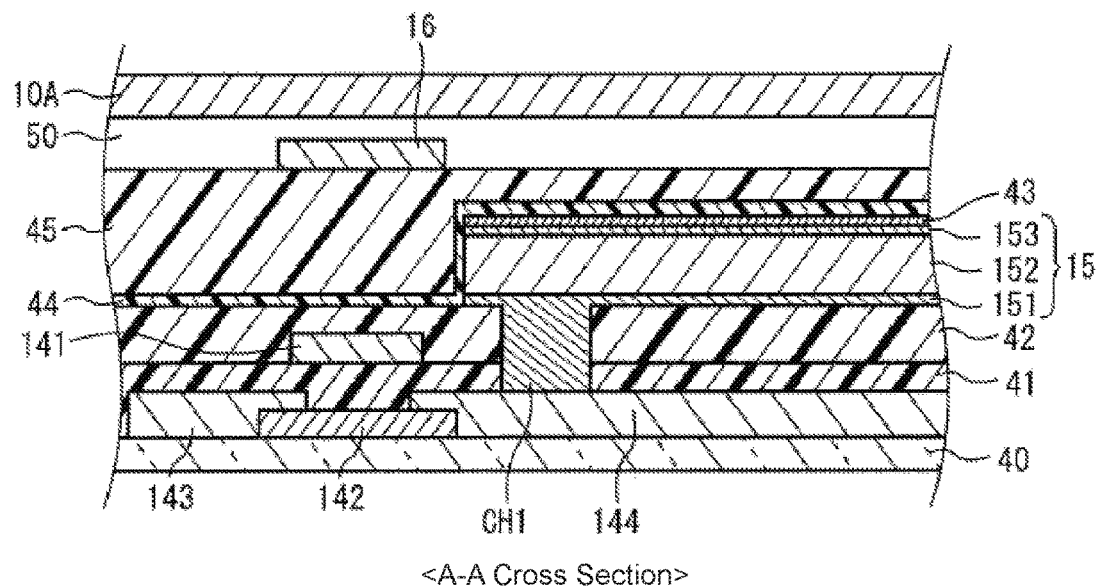
FIG. 14 is a cross-sectional view of a pixel of an imaging panel having a top-gate TFT according to a modification example.
Figure 15:
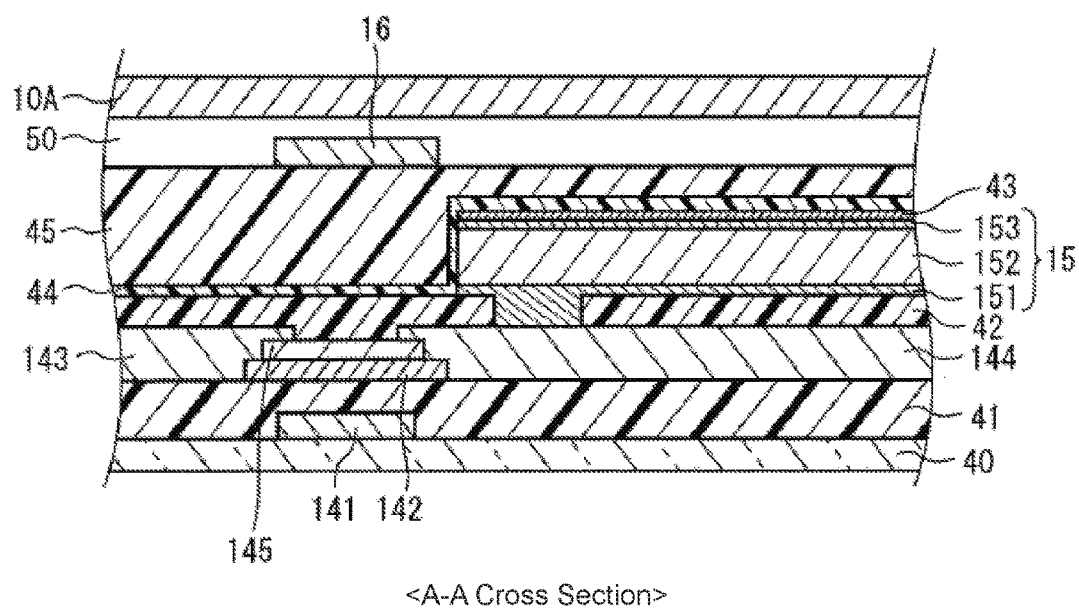
FIG. 15 is a cross-sectional view of a modification example of a pixel in the imaging panel including a TFT having an etch-stop layer.

In the embodiment described above, an example was described in which the bottom-gate TFT 14 is included in the imaging panel 10, but as shown in FIG. 14, the TFT may be a top-gate TFT, or a bottom-gate TFT such as that shown in FIG. 15, for example.

The parts that differ from the embodiment described above for the method of manufacturing an imaging panel having the top-gate TFT 14 shown in FIG. 14 will be explained below. First, the semiconductor active layer 142 made of an oxide semiconductor is formed on the substrate 40. Then, titanium, aluminum, and titanium are layered in this order on the substrate 40 and semiconductor active layer 142 to form the source electrode 143, data line 12, and drain electrode 144.

Next, the silicon oxide ($SiO_x$) or silicon nitride ($SiN_x$) etc. gate insulating film 41 is formed on the semiconductor active layer 142, source electrode 143, data line 12, and drain electrode 144. Thereafter, aluminum and titanium are layered on the gate insulating film 41 to form the gate electrode 141 and gate line 11.

After the gate electrode 141 is formed, the first interlayer insulating film 42 is formed on the gate insulating film 41 so as to cover the gate electrode 141, and the first contact hole CH1 is formed penetrating through to the drain electrode 144. Then, in a similar manner to the embodiment described above, the photodiode 15 is formed on the first interlayer insulating film 42 and the drain electrode 144.

Furthermore, in the case of an imaging panel equipped with a TFT 14 having an etch stop layer 145 as shown in FIG. 15, then in the above-mentioned embodiment, after the semiconductor active layer 142 is formed, plasma-enhanced CVD or the like is used to deposit silicon oxide ($SiO_2$) on the semiconductor active layer 142, for example. Thereafter, photolithography is used to pattern and form the etch stop layer 145. Then, after the etch stop layer 145 is formed, titanium, aluminum, and titanium may be layered in this order on the semiconductor active layer 142 and the etch stop layer 145 to form the source electrode 143, data line 12, and drain electrode 144.

An embodiment of the present invention has been described above, but the above embodiment is a mere example of an implementation of the present invention. Thus, the present invention is not limited to the embodiment described above, and can be implemented by appropriately modifying the embodiment described above without departing from the spirit of the present invention.

INDUSTRIAL APPLICABILITY

The present invention is useful for imaging panels and X-ray imaging devices.

What is claimed is:

1. An imaging panel for generating an image in accordance with scintillation light obtained from X-rays that have passed through a specimen, the imaging panel comprising:
    a substrate;
    a plurality of thin film transistors on the substrate;
    a first insulating film covering the thin film transistors;
    a plurality of conversion elements on the first insulating film that convert the scintillation light to electric charge;
    a second insulating film covering the plurality of conversion elements and the first insulating film, the second insulating film having a contact hole therein;
    a photosensitive resin layer on the second insulating film and in the contact hole of the second insulating film; and
    a bias wiring line respectively connecting to the conversion elements and supplying a bias voltage to the conversion elements,
    wherein each of the thin film transistors includes:
        a gate electrode;
        a gate insulating film in a layer above or a layer below the gate electrode;
        a semiconductor active layer facing the gate electrode with the gate insulating film interposed between the semiconductor active layer and the gate electrode;
        a source electrode electrically connected to the semiconductor active layer; and
        a drain electrode electrically connected to the semiconductor active layer and separated from the source electrode,
    wherein the plurality of conversion elements each include:
        a first semiconductor layer electrically connected to the drain electrode via a contact hole in the first insulating film;
        a second semiconductor layer over the first semiconductor layer and having a conductivity type that is opposite to the first semiconductor layer; and
        an electrode on the second semiconductor layer, and
    wherein a contact hole is formed in a portion of the photosensitive resin layer that is disposed within said contact hole in the second insulating film, and said electrode on the second semiconductor layer is connected to the bias wiring line via said contact hole in said portion of the photosensitive resin layer.

2. The imaging panel according to claim 1, wherein, in the contact hole, a periphery of the contact hole in the second insulating film is covered by the photosensitive resin layer.

3. The imaging panel according to claim 1, wherein the gate insulating film is in a layer above the gate electrode.

4. The imaging panel according to claim 3, further comprising an etch-stop layer on the semiconductor active layer.

5. The imaging panel according to claim 1, wherein the gate insulating film is in a layer below the gate electrode.

6. An X-ray imaging device, comprising:
    the imaging panel according to claim 1;
    a controller controlling respective gate voltages of the plurality of thin film transistors and reading out data signals that correspond to electric charge converted by the conversion elements;
    an X-ray light source radiating X-rays; and
    a scintillator converting the X-rays to scintillation light.

7. The imaging panel according to claim 2, wherein the gate insulating film is in a layer above the gate electrode.

8. The imaging panel according to claim 7, further comprising an etch-stop layer on the semiconductor active layer.

9. The imaging panel according to claim 2, wherein the gate insulating film is in a layer below the gate electrode.

* * * * *